(12) United States Patent
Hsu et al.

(10) Patent No.: US 12,207,864 B2
(45) Date of Patent: Jan. 28, 2025

(54) SURGICAL DEVICE AND METHODS

(71) Applicant: AULEA MEDICAL, INC., San Ramon, CA (US)

(72) Inventors: George Chao-chih Hsu, San Ramon, CA (US); Csaba Truckai, Saratoga, CA (US)

(73) Assignee: AULEA MEDICAL, INC., San Ramon, CA (US)

( * ) Notice: Subject to any disclaimer, the term of this patent is extended or adjusted under 35 U.S.C. 154(b) by 0 days.

(21) Appl. No.: 18/594,942

(22) Filed: Mar. 4, 2024

(65) Prior Publication Data
US 2024/0206957 A1 Jun. 27, 2024

Related U.S. Application Data

(63) Continuation of application No. 17/820,349, filed on Aug. 17, 2022, now abandoned, which is a
(Continued)

(51) Int. Cl.
*A61B 18/00* (2006.01)
*A61B 18/14* (2006.01)
(Continued)

(52) U.S. Cl.
CPC ........ *A61B 18/1482* (2013.01); *A61B 18/149* (2013.01); *A61B 2018/00083* (2013.01);
(Continued)

(58) Field of Classification Search
None
See application file for complete search history.

(56) References Cited

U.S. PATENT DOCUMENTS 5,250,047 A  10/1993  Rydell
5,354,302 A * 10/1994  Ko .................... A61B 1/00087
                                                    604/161
(Continued)

FOREIGN PATENT DOCUMENTS

WO     2016204997 A1    12/2016
WO     2019094643 A1    5/2019
(Continued)

OTHER PUBLICATIONS

International Search Report and Written Opinion for PCT/US2018/059897, mailed on Jan. 17, 2019.
(Continued)

*Primary Examiner* — Linda C Dvorak
*Assistant Examiner* — Nicholas S Borsch
(74) *Attorney, Agent, or Firm* — Dorsey & Whitney LLP

(57) ABSTRACT

A tissue resecting or other medical device includes a handle coupled to an elongated shaft. A radiofrequency (RF) electrode is carried at a distal end of the elongated shaft, and the electrode is moveable across a window in a sleeve or other component of the shaft. The shaft has an interior channel connectable to a negative pressure source to remove debris from the channel. A motor is carried by the handle and operatively coupled to the electrode for moving the electrode relative to the window. An electronic image sensor and lens are disposed at a distal end of the shaft, and a plurality of conductors may extend through the shaft to the image sensor. The image sensor, lens and sensor conductors are disposed within a first tubular member, and an LED or other light source is also positioned at a distal end of the shaft with LED conductors or leads extending through a second tubular member of the shaft to the LED.

19 Claims, 13 Drawing Sheets

Related U.S. Application Data continuation of application No. 16/260,815, filed on Jan. 29, 2019, now Pat. No. 11,446,080.

(60) Provisional application No. 62/719,544, filed on Aug. 17, 2018, provisional application No. 62/690,826, filed on Jun. 27, 2018, provisional application No. 62/623,656, filed on Jan. 30, 2018.

(51) Int. Cl.
  *A61B 90/00* (2016.01)
  *A61B 90/30* (2016.01)

(52) U.S. Cl.
  CPC ............ *A61B 2018/00136* (2013.01); *A61B 2018/00196* (2013.01); *A61B 2018/00208* (2013.01); *A61B 2018/00517* (2013.01); *A61B 2018/00547* (2013.01); *A61B 2018/00601* (2013.01); *A61B 2018/00875* (2013.01); *A61B 2018/00982* (2013.01); *A61B 2018/1405* (2013.01); *A61B 2018/1452* (2013.01); *A61B 2018/147* (2013.01); *A61B 2090/064* (2016.02); *A61B 2090/309* (2016.02); *A61B 90/36* (2016.02); *A61B 2218/002* (2013.01); *A61B 2218/007* (2013.01)

(56) References Cited

U.S. PATENT DOCUMENTS

| | | | |
|---|---|---|---|
| 5,752,970 A | 5/1998 | Yoon | |
| 5,824,002 A | 10/1998 | Gentelia et al. | |
| 5,906,615 A | 5/1999 | Thompson | |
| 6,358,238 B1 | 3/2002 | Sherry | |
| 6,508,825 B1 | 1/2003 | Selmon et al. | |
| 6,537,288 B2 | 3/2003 | Vargas et al. | |
| 6,770,026 B2 | 8/2004 | Kan et al. | |
| 6,939,318 B2 | 9/2005 | Stenzel | |
| 7,056,329 B2 | 6/2006 | Kerr | |
| 7,604,648 B2 | 10/2009 | Kerr | |
| 7,744,595 B2 | 6/2010 | Truckai et al. | |
| 8,221,404 B2 | 7/2012 | Truckai | |
| 8,262,619 B2 | 9/2012 | Chebator et al. | |
| 8,337,394 B2 | 12/2012 | Vakharia | |
| 8,622,894 B2 | 1/2014 | Banik et al. | |
| 9,056,182 B2 | 6/2015 | Moulton et al. | |
| 9,308,077 B2 | 4/2016 | Behan et al. | |
| 9,839,473 B2 | 12/2017 | Germain et al. | |
| 9,848,947 B2 | 12/2017 | Sukthankar et al. | |
| 9,980,715 B2 | 5/2018 | Marino et al. | |
| 10,004,556 B2 | 6/2018 | Orczy-Timko et al. | |
| 10,383,682 B2 | 8/2019 | Sartor et al. | |
| 10,675,087 B2 | 6/2020 | Truckai et al. | |
| 10,736,491 B2 | 8/2020 | Truckai | |
| 10,758,301 B2 | 9/2020 | Ciccone et al. | |
| 10,869,716 B2 | 12/2020 | Sartor et al. | |
| 10,939,933 B2 | 3/2021 | Truckai | |
| 11,141,045 B2 | 10/2021 | Kucharski et al. | |
| 11,246,649 B2 | 2/2022 | Germain et al. | |
| 11,246,650 B2 | 2/2022 | Germain et al. | |
| 11,272,835 B2 | 3/2022 | Hsu et al. | |
| 11,304,747 B2 | 4/2022 | Simani et al. | |
| 11,446,080 B2 | 9/2022 | Hsu et al. | |
| 11,497,551 B2 | 11/2022 | Germain et al. | |
| 11,648,048 B1 | 5/2023 | Barry et al. | |
| 11,672,593 B2 | 6/2023 | Germain et al. | |
| 11,707,182 B2 | 7/2023 | Weeks et al. | |
| 11,717,342 B2 | 8/2023 | Willhite et al. | |
| 11,723,681 B2 | 8/2023 | Germain et al. | |
| 11,826,023 B2 | 11/2023 | Craig et al. | |
| 11,883,053 B2 | 1/2024 | Germain et al. | |
| 11,944,276 B2 | 4/2024 | Hsu et al. | |
| 2002/0042622 A1 | 4/2002 | Vargas et al. | |
| 2002/0111564 A1 | 8/2002 | Burbank et al. | |
| 2003/0181905 A1 | 9/2003 | Long | |
| 2004/0073088 A1 | 4/2004 | Friedman et al. | |
| 2004/0073195 A1 | 4/2004 | Cucin | |
| 2004/0082969 A1 | 4/2004 | Kerr | |
| 2004/0138655 A1 | 7/2004 | McClurken et al. | |
| 2005/0010203 A1 | 1/2005 | Edwards et al. | |
| 2005/0070889 A1* | 3/2005 | Nobis | A61B 17/320016 606/45 |
| 2005/0234294 A1 | 10/2005 | Saadat et al. | |
| 2005/0272975 A1 | 12/2005 | McWeeney et al. | |
| 2007/0021656 A1 | 1/2007 | Martin et al. | |
| 2007/0051375 A1 | 3/2007 | Milliman | |
| 2007/0213704 A1 | 9/2007 | Truckai et al. | |
| 2007/0244440 A1 | 10/2007 | Pal et al. | |
| 2008/0097476 A1 | 4/2008 | Peh et al. | |
| 2008/0161902 A1 | 7/2008 | Poulsen | |
| 2008/0249553 A1 | 10/2008 | Gruber et al. | |
| 2009/0018603 A1 | 1/2009 | Mitelberg et al. | |
| 2009/0076329 A1* | 3/2009 | Su | A61B 1/00193 600/166 |
| 2009/0270849 A1 | 10/2009 | Truckai et al. | |
| 2010/0081877 A1 | 4/2010 | Vakharia | |
| 2010/0249602 A1 | 9/2010 | Buckley et al. | |
| 2010/0305565 A1 | 12/2010 | Truckai et al. | |
| 2011/0028898 A1 | 2/2011 | Clark et al. | |
| 2011/0160539 A1 | 6/2011 | Robertson | |
| 2012/0083740 A1 | 4/2012 | Chebator et al. | |
| 2012/0323180 A1 | 12/2012 | Chebator et al. | |
| 2012/0330292 A1* | 12/2012 | Shadduck | A61B 18/1206 606/29 |
| 2013/0046304 A1 | 2/2013 | Germain et al. | |
| 2013/0090642 A1 | 4/2013 | Shadduck et al. | |
| 2013/0172870 A1 | 7/2013 | Germain et al. | |
| 2013/0231652 A1 | 9/2013 | Germain et al. | |
| 2014/0200398 A1 | 7/2014 | Hawkins et al. | |
| 2014/0236088 A1 | 8/2014 | Al-Rashdan et al. | |
| 2014/0236122 A1 | 8/2014 | Anderson et al. | |
| 2014/0257269 A1 | 9/2014 | Woloszko et al. | |
| 2014/0276908 A1 | 9/2014 | Raybin et al. | |
| 2014/0303611 A1 | 10/2014 | Shadduck et al. | |
| 2014/0324065 A1 | 10/2014 | Bek et al. | |
| 2014/0336643 A1 | 11/2014 | Orczy-Timko et al. | |
| 2015/0105791 A1 | 4/2015 | Truckai | |
| 2015/0157387 A1 | 6/2015 | Ouyang et al. | |
| 2015/0157396 A1 | 6/2015 | Germain et al. | |
| 2015/0230697 A1 | 8/2015 | Phee et al. | |
| 2015/0250992 A1 | 9/2015 | Morriss et al. | |
| 2016/0089184 A1 | 3/2016 | Truckai et al. | |
| 2016/0095615 A1 | 4/2016 | Orczy-Timko et al. | |
| 2016/0106562 A1 | 4/2016 | Puckett et al. | |
| 2016/0228116 A1 | 8/2016 | Milliman | |
| 2016/0235279 A1 | 8/2016 | Yamakawa | |
| 2017/0014252 A1 | 1/2017 | Kelly | |
| 2017/0035274 A1 | 2/2017 | Mikkaichi | |
| 2017/0086918 A1 | 3/2017 | Shadduck et al. | |
| 2017/0105507 A1 | 4/2017 | Golding | |
| 2017/0105607 A1 | 4/2017 | Truckai | |
| 2017/0105748 A1 | 4/2017 | Truckai | |
| 2017/0181793 A1 | 6/2017 | Germain et al. | |
| 2017/0258519 A1* | 9/2017 | Germain | A61B 18/1482 |
| 2017/0265892 A1 | 9/2017 | Winegar et al. | |
| 2017/0333119 A1 | 11/2017 | Truckai | |
| 2017/0333120 A1 | 11/2017 | Truckai | |
| 2018/0036156 A1 | 2/2018 | Kelly | |
| 2018/0071015 A1 | 3/2018 | Germain et al. | |
| 2018/0221054 A1 | 8/2018 | Truckai | |
| 2018/0280077 A1 | 10/2018 | Orczy-Timko et al. | |
| 2019/0133676 A1 | 5/2019 | Hsu et al. | |
| 2019/0231416 A1 | 8/2019 | Hsu et al. | |
| 2021/0059748 A1 | 3/2021 | Hsu et al. | |

(56) References Cited

U.S. PATENT DOCUMENTS

2022/0322926 A1  10/2022  Hsu et al.
2023/0181239 A1   6/2023  Hsu et al.

FOREIGN PATENT DOCUMENTS

WO      2019152377 A1   8/2019
WO      2022031851 A2   2/2022

OTHER PUBLICATIONS

International Search Report and Written Opinion for PCT/US2021/044545, mailed on Feb. 1, 2022.
"Extended European Search Report for EP19748025.4, mailed on Sep. 17, 2021".
"International Search Report and Written Opinion for PCT/US2019/015585, mailed on Apr. 26, 2019".
U.S. Appl. No. 18/615,481, titled "Surgical Device and Methods", filed Mar. 25, 2024, pp. all pages of application as filed.
Extended European Search Report for European Patent Application No. EP21853253.9, mailed Jul. 22, 2024, pp. all.
Anonymous, "Coaxial cable", Wikipedia, Jul. 28, 2020, XP093183155, retried from the Internet: URL: https://en.wikipedia.org/w/index/php?title=coaxial_cable&oldid=969906879.
Extended European Search Report for EP Appl. No. 24151142.7, mailed on Feb. 20, 2024.
"Examination Report for EP19748025.4, mailed on Jul. 23, 2023 pp. all".

* cited by examiner

SURGICAL DEVICE AND METHODS

CROSS-REFERENCE TO RELATED APPLICATIONS

The present application is a continuation of U.S. patent application Ser. No. 17/820,349, filed Aug. 17, 2022, which is a continuation of U.S. patent application Ser. No. 16/260,815, filed Jan. 29, 2019, as issued as U.S. Pat. No. 11,446,080, on Sep. 20, 2022, which claims the benefit of provisional application No. 62/719,544, filed on Aug. 17, 2018; of provisional application No. 62/690,826, filed on Jun. 27, 2018; and of provisional application No. 62/623,656, filed on Jan. 30, 2018, the full disclosures of which are incorporated herein by reference.

BACKGROUND OF THE INVENTION

1. Field of the Invention

The present invention relates to devices and methods for resecting and removing tissue from an interior of a patient's body, for example in a transurethral resection of prostate tissue to treat benign prostatic hyperplasia.

Electrosurgical cutting devices often comprise a shaft or sleeve having a tissue extraction lumen with one or more radio frequency (RF) cutting blades arranged to resect tissue which may then be drawn into the extraction lumen, often via vacuum assistance through a cutting window. Most such electrosurgical tissue cutting devices rely on manually engaging the cutting window against the target tissue to be resected. While such manual engagement is often sufficient, in other cases, such as in laparoscopic procedures having limited access and field of view, the target tissue can be difficult to visualize prior to resection and, in particular, it can be difficult to assure that the optimum target site has been engaged by the cutting window. For these reasons, it would be desirable to provide improved electrosurgical cutting tools having improved visibility and ability engage and immobilize tissue prior to cutting and to extract the tissue from tools after cutting.

For resection of remote tissue sites, such as the prostate, it is usually desirable to introduce the surgical cutter through a tubular introducer device. Though such tubular introducers can be advanced "blind," i.e., without direct optical visualization, it is frequently advantageous to provide such introducers with direct visualization. For example, it would be desirable to use an endoscope to observe the urethra while transurethrally advancing an introducer sheath for subsequent resection of the prostate. Once the introducer sheath is in place and the surgical cutter has been introduced, however, it will still be necessary to move a cutter element on the surgical cutter to resect the tissue. Heretofore, this has typically been accomplished by manually reciprocating a cutter assembly on the tissue resecting apparatus. Manual resection, while generally effective, can be difficult to control and, in particular, can be difficult to coordinate with other aspects of the resection procedure, such as applying RF power, applying a vacuum to aspirate tissue fragments and debris, and the like.

For these reasons, it would be desirable to provide improved apparatus, systems and methods for resecting tissue in prostatectomies and other procedures. It would be particularly desirable to provide apparatus, systems and methods which provide improved control of tissue resection including but not limited to enhanced coordination of cutter movement control, cutting power control, vacuum aspiration control, and the like. At least some of these objectives will be met by the inventions described below.

2. Listing of Background Art

Related patents and published applications include U.S. Pat. Nos. 8,221,404; 7,744,595; U.S. Pat. Publ. 2014/0336643; U.S. Pat. Publ. 2010/0305565; U.S. Pat. Publ. 2007/0213704; U.S. Pat. Publ. 2009/0270849; U.S. Pat. Publ. 2013/0090642; U.S. Pat. Publ. 2013/0046304; U.S. Pat. Publ. 2013/0172870; U.S. Pat. Publ. 2015/0105791; U.S. Pat. Publ. 2015/0157396; U.S. Pat. Publ. 2016/0089184; U.S. Pat. Publ. 2016/0095615; U.S. Pat. Publ. 2017/0086918; U.S. Pat. Publ. 2017/0181793; and U.S. Pat. Publ. 2018/0071015. See also commonly assigned, published applications: U.S. Pat. Publ. 2014/0336643; U.S. Pat. Publ. 2017/0105748; U.S. Pat. Publ. 2017/0105607; U.S. Pat. Publ. 2017/0333120; U.S. Pat. Publ. 2017/0333119; U.S. Pat. Publ. 2018/0221054; and U.S. Pat. Publ. 2018/0280077.

SUMMARY OF THE INVENTION

The present invention provides apparatus, systems, and methods for performing electrosurgical resections in minimally invasive procedures. While the apparatus, systems, and methods are particularly suitable for performing transurethral resection of the prostate (often referred to as TURP), they will also find use in a variety of other laparoscopic and other endoscopic and endosurgical procedures. The apparatus comprises motor-driven cutters, where the motors are configured to drive both a shaft of the cutter and a cutter electrode, either independently, contemporaneously, or selectively independently and contemporaneously. The systems comprise the cutters together with a digital or other controller configured to coordinate movements of the shaft, electrodes, and other external components such as a radiofrequency power supply (e.g. by selecting a cutting or a coagulation waveform, power, timing, etc.), a negative pressure source, and the like. The methods of the present invention comprise using the apparatus and systems as just described for prostatectomies and other tissue resection procedures.

In a first aspect, the present invention provides a tissue resecting device comprising a shaft assembly movably attached to a handle and having a longitudinal axis. A housing is secured to a distal end of the shaft and has a window configured to be fluidly coupled to a negative pressure source. An electrode is disposed in the housing and configured to move relative to the window, and a motor in the handle is adapted to move the electrode across the window.

In an additional specific example, the motor will be adapted to move the electrode at a fixed speed or rate relative to the window, e.g. at a rate greater than 1 cycle per second (CPS), often greater than 5 CPS.

The shaft may be operated manually. That is, the user may be able to manually initiate the at least one motor to move the electrode in the housing relative to the window and then manually reciprocate the shaft in an axial stroke relative to the handle. Even when being operated manually, the tissue resecting device will usually be operated through an interface (typically including a radiofrequency (RF) power supply) which may provide for specific operational parameters, often fixed or manually adjustable parameters, such as stroke times, power levels, RF waveforms, and the like, without having feedback control capability.

Often, the tissue resecting device will be provided as part of a tissue resecting system which further comprises a controller which is configured to operate not only the motor, but usually also a RF power source which is coupled to the electrode and also a negative pressure source which may be coupled to the window in the housing. The controller may be further configured or adapted to automatically or manually control at least one motor to stop movement of the electrode in a selected position relative to the window. Alternatively or additionally, the controller may be adapted to stop the electrode in the center of the window. Alternatively or additionally, the controller may be adapted to stop the electrode at an end of the window.

The controller may be adapted in a variety of other different control protocols. For example, the controller may be adapted to control the motor to provide a single movement cycle of the electrode back and forth across the window. That is, the user may be able to cause the controller to initiate only a single pass of the electrode over the window in order to achieve a controlled cutting of tissue. Additionally, the controller will usually be configured to control and coordinate the delivery of negative pressure from the negative pressure source to the housing window and to actuate the at least one motor, usually contemporaneously.

In still further aspects of the systems of the present invention, the controller may be configured to modulate the negative pressure source in response to movement of the electrode relative to the window. For example, the controller may be configured to active or deactivate the RF source in response to movement of the electrode relative to the window. Still additionally, the controller may be configured to activate or deactivate the RF source to deliver a cutting current waveform or a coagulation waveform to the electrode.

In particular aspects of the present invention as described in detail below, the devices, systems and methods are particularly configured for treating the prostate, optionally under endoscopic visualization. For example, the systems may comprise a RF source configured to deliver RF current alternatively in a cutting waveform and a coagulation waveform to the electrode, a motor configured to move the electrode, and a controller configured to operate the motor and RF source in a first mode delivering a cutting waveform while activating the motor to move the electrode in a second mode delivering a coagulation waveform after de-activating the motor to stop the electrode in a selected stationary position. Such methods for treating the prostate may comprise providing a treatment device with a shaft extending along a longitudinal axis to a distal portion having a window communicating with an aspiration source and a motor driven electrode adapted to move relative to the window. The window is engaged against targeted prostate tissue, and the RF source is operated in a first mode with a cutting waveform delivered to the electrode while activating the motor to move the electrode to resect tissue and thereafter operated in a second mode with a coagulation waveform delivered to the electrode after de-activating the motor to stop the electrode in a selected stationary position to coagulate tissue.

In one particular aspect of the present invention, a tissue imaging and resection device comprises a handle and an introducer sleeve attachable to the handle. Typically, the handle will be permanently affixed to the introducer sleeve, but in other embodiments the handle and introducer sleeve could be detachable. The tissue imaging and resection device further comprises an axially translatable resecting component disposed within the introducer sleeve assembly. The axially translatable resecting component typically has a working end disposed at a distal end thereof where the working end usually includes an electrosurgical or other cutting implement configured to resect tissue. The tissue imaging and resection device will typically further comprise a tubular assembly disposed within the introducer sleeve and having an electronic imaging sensor, a lens, and a light source, disposed at a distal end of the tubular assembly.

In particular aspects of the tissue imaging and resection device, the handle will often carry a motor which is operatively coupled to the resecting component for driving a movable tissue resection element, such as an electrode, blade, or the like, in the resecting component. In specific embodiments, the tissue resection element comprises a radio frequency (RF) electrode of a type that can be connected to a radiofrequency power supply which delivers a cutting current to the electrode in order to allow the electrode to resect tissue as it is advanced there through. In such instances, the tissue imaging and resection device will typically include electromagnetic (EM) shielding between the electronic image sensor and the RF electrode. For example, the electronic image sensor and associated electrical leads may be encased in an electrically conductive tube, cylinder, or elongate hollow structure, typically a metal tube, which is covered with a polymeric or other electrically insulating layer, such as a shrink wrap tubing, over its exterior surface with a similar insulating layer typically over a lens component coupled to the image sensor.

In still further instances, the introducer sleeve of the tissue imaging and resection devices of the present invention will have a proximal and, a distal end, and a central passage extending along an axis between the proximal and distal ends. In these embodiments, the axially translatable resecting component typically comprises a shaft extending axially through the central passage of the introducer sleeve. The shaft will typically have a resection window near its distal end and an aspiration channel extending from the resection window to a proximal location on the shaft. The proximal location will usually lie within the handle and be configured for coupling to a negative pressure source via a connection in the handle.

In further specific instances, the tubular assembly may comprise at least one tubular member disposed in parallel to the shaft of the axially translatable resecting component within the central passage of the introducer sleeve. The tubular assembly may comprise a single tubular member which carries each of the electronic imaging sensor, lens, and the light source. More typically, however, the tubular assembly will comprise a first tubular member which carries the lens and the electronic imaging sensor and a second tubular member which carries the light source. By separating the imaging components from the light source, e.g. placing only the imaging sensor and associated conductor leads within one electromagnetically isolated structure as described above, and placing the light source in a tubular or other structure, the first and second tubular members may be have a total cross-sectional area that is less than a single tubular member and such first and second tubular members may be isolated from one another by electromagnetic shielding to inhibit or prevent interference between the relatively high power light source and the low power imaging sensor. For example, the light source may comprise a light emitting diode (LED) at a distal end of the second tubular member with LED conductor leads extending from a proximal location on the second tubular member to the LED. The first tubular member may further comprise sensor conductors extending from a proximal location thereon to the electronic image sensor. In particular configurations, the sensor conductors are coupled to a circuit board, and all sides and a distal end of the first tubular member are encased in components providing electromagnetic shielding of the image sensor and sensor conductors. In such instances, at least a distal portion of the electromagnetic shielding in the field of view of the lens will be transparent of the lens may be configured to provide such shielding.

In still other specific instances of the tissue imaging and resection devices of the present invention, at least a portion of the second tubular member will be encased in electromagnetic shielding. In such instances, at least a distal portion of the electromagnetic shielding on the second tubular member will also be transparent in order to allow the projection of light from the light source there through.

In still other specific aspects, the present invention provides devices, tools, systems, and methods for electrosurgical treatment of tissue, particularly for performing urological procedures such as resecting prostate tissue, resecting bladder tissue, and the like. The devices and tools of the present invention can be made with very low profiles, typically with diameters or widths at or below 10 mm, often below 6 mm, and frequently as low as 4 mm or less. The low profile devices and tools of the present invention are particularly advantageous as they can be configured to incorporate movable electrodes and other cutters, vacuum-assisted tissue extraction lumens, and other desirable features within the limited tool sizes available.

In one particular aspect, the tissue resection component, comprises an elongated shaft having an electrode assembly at or near a distal end thereof. The elongated shaft has a tissue-receiving window in a working end thereof, where the tissue-receiving window opens to a tissue-extraction lumen which extends along a longitudinal axis of the shaft. The electrode assembly includes a movable electrode which extends in a lateral direction over an exterior of the tissue-receiving window. The electrode assembly is configured to reciprocate the moveable electrode axially over an exterior region of the tissue-receiving window to resect tissue which is drawn inwardly into or through the window, typically by applying a vacuum or negative-pressure to the tissue extraction lumen. The moveable electrode has first and second lateral portions or sides that extend over first and second lateral edges of the tissue-receiving window, thus improving the ability of the electrode to resect or sheer tissue that is received through the window.

The moveable electrode may have a total surface area which is very low, typically in the range from 0.05 $in^2$ to 0.25 $in^2$. In more specific aspects, the electrode has a surface area less than 0.2 $in^2$, often less than 0.15 $in^2$, and in some instances less than 0.1 $in^2$. In such embodiments, the window will typically have an open area in the range from 8 $mm^2$ to 16 $mm^2$.

In still other aspects of the present invention, the electrode assembly is configured to reciprocate the moveable electrode with a stroke that extends over proximal and distal edges of the tissue-receiving window. By thus having the movable electrode extend over both the lateral edges and the proximal and distal edges of the tissue receiving window, complete resection of the tissue can be achieved.

In still further specific aspects of the present invention, the electrode assembly comprises a sleeve disposed externally on the electrode shaft, typically over an axial path along an outer cylindrical surface of the shaft. A longitudinal wire member is mounted to reciprocate within a lumen of the external sleeve, and a distal end of the longitudinal wire is attached to or integrated with the first lateral portion of the moveable electrode. Exemplary movable electrodes may thus comprise a lateral extension of the longitudinal electrode wire, e.g. in a hockey stick configuration. As described in more detail below, the lateral extension will typically be curved so that the electrode follows a curved envelope defined by the window which may be in a cylindrical wall of the working end or often in a curved surface that is offset outwardly from the cylindrical surface of the shaft.

The working end of the device may further comprise a ledge adjacent the second lateral edge of the tissue-receiving window and a distal tip of the second lateral portion of the moveable electrode may travel along a surface of the ledge as the moveable electrode is reciprocated.

In still further aspects of the present invention, the tissue-receiving window is formed in a curved surface of dielectric housing and such a curved surface is outward and asymmetric relative to a cylindrical surface of the shaft. The moveable electrode typically has an arcuate shape with a curvature that conforms to the curvature of the tissue-receiving window.

In still other specific aspects of the present invention, the tissue resecting devices may further comprise a handle attachable to a proximal end of the elongated shaft. The motor drive assembly is typically disposed within the handle. The motor drive assembly may be adapted to axially reciprocate the moveable electrode across the window in the range of 1 Hz to 50 Hz.

Typically, the tissue resecting devices of the present invention will be present in systems comprising a controller adapted to control the motor drive assembly, the negative pressure source, and energy delivery to the movable electrode.

In still other specific aspects of the present invention, the window edges may comprise a dielectric material. For example, the working end may comprise a dielectric housing with the tissue-receiving window disposed in the dielectric housing. In such instances, the lateral edges as well as the proximal and distal edges of the tissue-receiving window will be formed from the dielectric material. The dielectric material may be any one or more of a polymer, a ceramic, a glass, or other suitable dielectric materials.

DETAILED DESCRIPTION OF THE INVENTION

Figure 1:
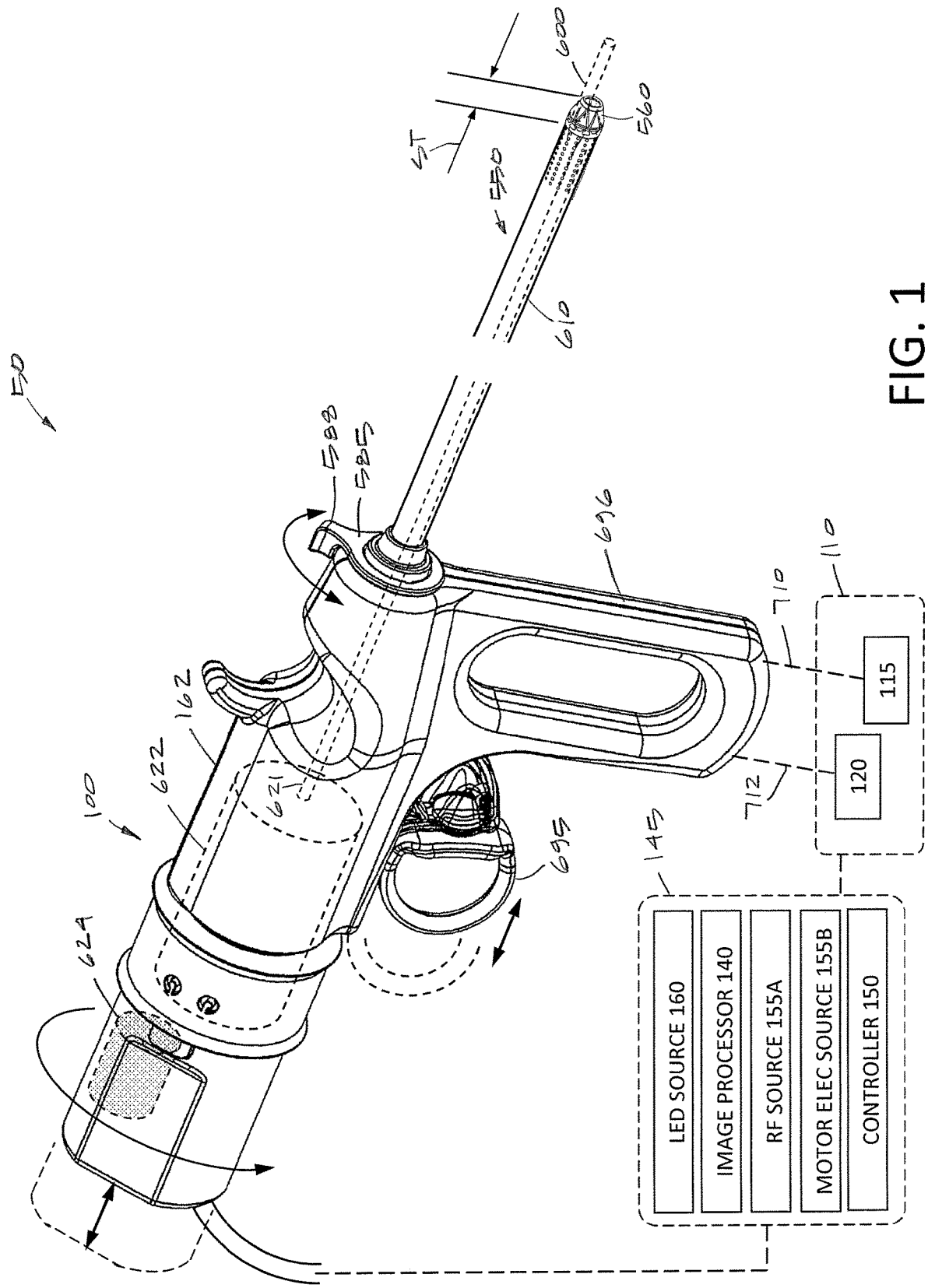
FIG. 1 is a view of a tissue resecting system and a block diagram of systems and operating components corresponding to the invention.
Figure 2:
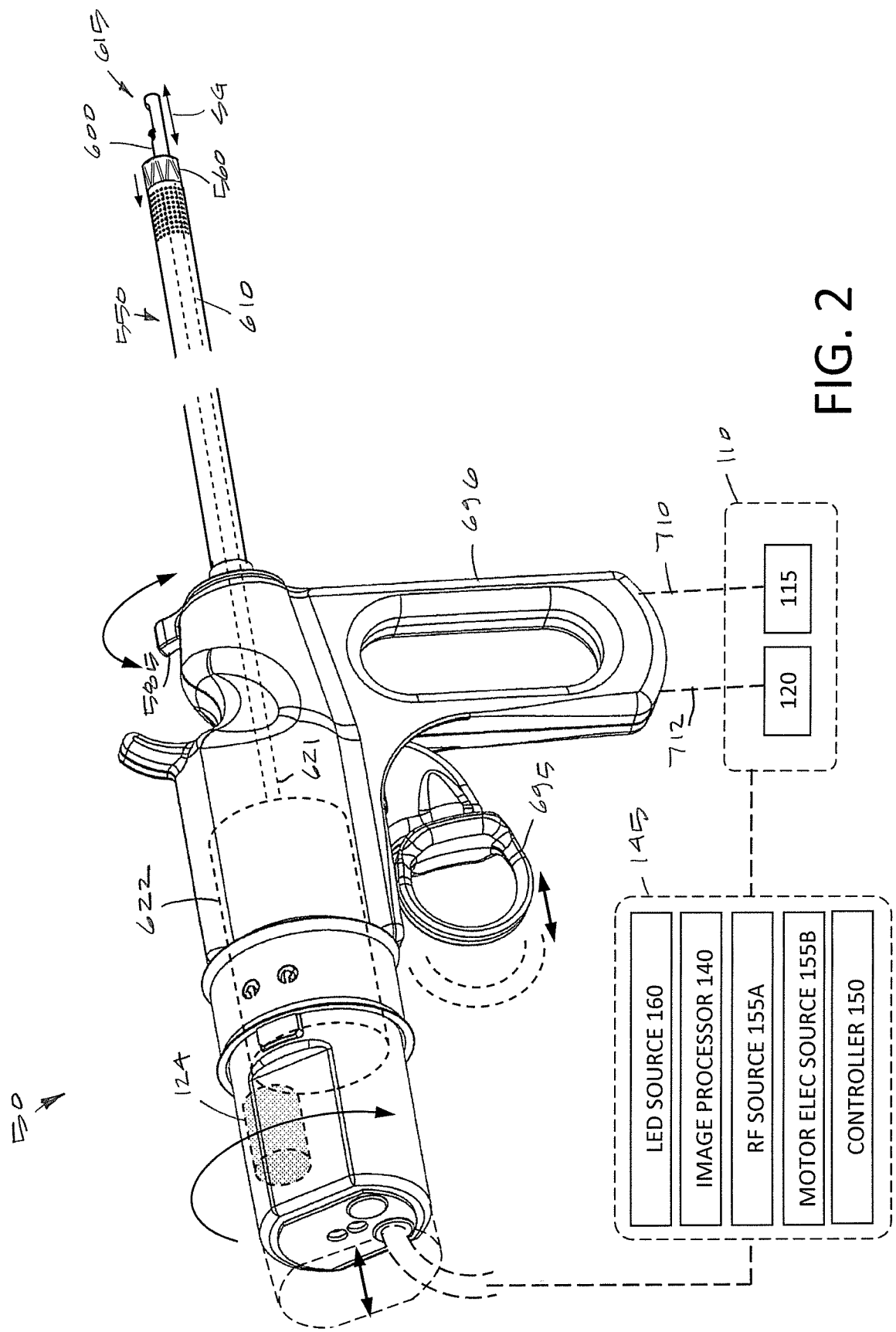
FIG. 2 is another perspective view of the system of FIG. 1 from a different angle showing the working end of a tissue-resecting component extending distally from an outer sleeve of the device.

FIGS. 1-2 illustrate an endoscopic, electrosurgical tissue resecting system 50 for use in urological procedures to resect tissue. The system 50 includes a hand-held resecting device 100 and fluid management system 110 consisting of a fluid source 115 for providing fluid inflows or irrigation to a working space and a negative pressure source 120 for aspirating fluids from the working space.

Figure 4A:
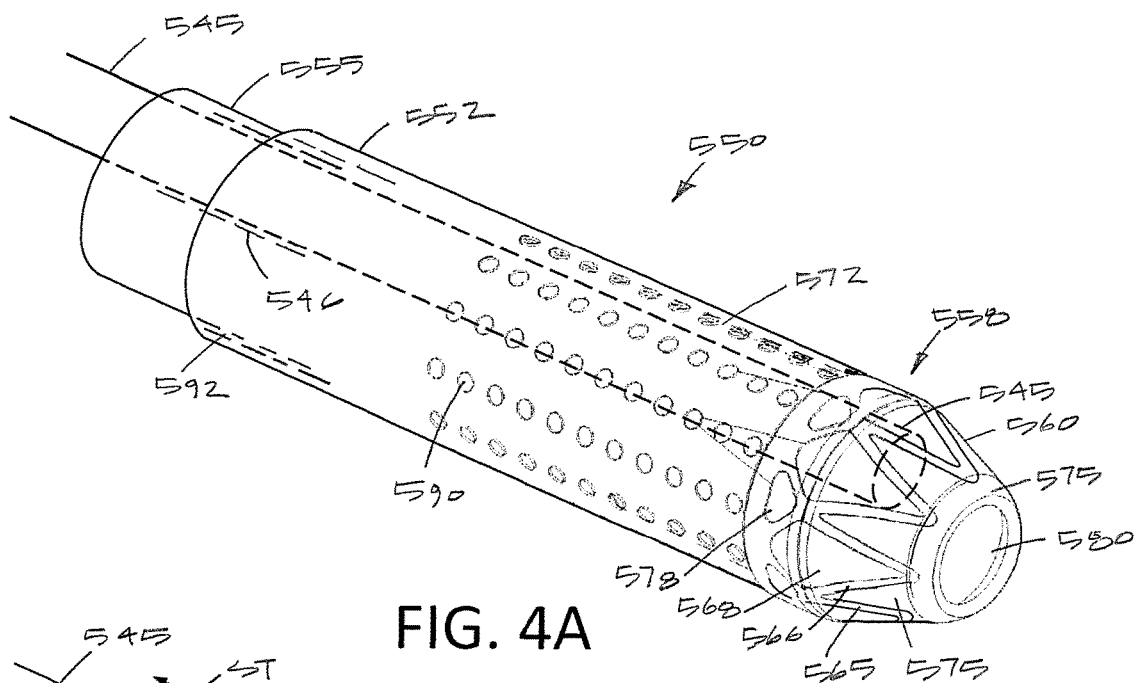
FIG. 4A is an enlarged view of the distal end portion of the resecting device of FIGS. 1-2 showing an expandable, resilient structure in a tapered shape for introduction into a patient's body.

The resecting device 100 is a single-use tissue device or probe including a single-use viewing system consisting of a distal electronic imaging sensor 125 (with lens 130) coupled to an imaging processor 140 in a console or base unit 145 (see FIGS. 1 and 4A). The base unit 145 may optionally carry the fluid management system 110. Additionally, the base unit 145 may carry a microprocessor or controller 150 for controlling all operating parameters of the fluid management system 110, an RF source 155A for energizing the electrosurgical component, an electrical source 155B coupled to a motor drive unit described further below and an LED source 160 for delivering electrical current to at least one LED described further below.

The resecting device 100 has a handle portion 162 that is coupled to an elongated shaft or introducer sleeve assembly 550 that has an outer diameter ranging from about 5 mm to 10 mm, and in one variation is approximately 7 mm in diameter. In a variation, the device is adapted for performing a TURP procedure (transurethral resection of prostate) or a bladder tumor resection procedure and thus the shaft portion has a length suitable for introducing in a transurethral approach to reach the targeted prostate tissue or bladder tissue.

The tissue resecting system 50 includes four functional components which will be described separately. First, the system includes introducer sleeve component that has a soft tapered tip for introducing through body passageway under endoscopic vision wherein the sleeve can be adjusted to a cylindrical, non-tapered shape for advancing the resecting component therethrough. Second, the system 50 includes the RF tissue resecting component with a motor-driven moveable electrode. Third, the system 50 includes the fluid management component 110 as indicated above. Fourth, the system includes an endoscopic viewing component.

As can be understood in FIGS. 1, 2, 4A-4B, the resecting device 100 has an integrated introducer sleeve assembly 550 which consists of an outer introducer sleeve or tubular member 552 and an inner sleeve 555 described further below. FIGS. 1-2 show the outer sleeve 552 fixed to the handle 162 which extends to a distal end 558 and which includes a resilient structure 560 that is movable or deformable between a first tapered, rounded-nose shape or configuration (FIG. 4A) for introduction through a body passageway and a second cylindrical shape or configuration (FIG. 4B) that allows for the endoscope sleeve 545 and resecting component 600 to be advanced into or through the distal end of the sleeve assembly 550 and resilient structure 560. The outer introducer sleeve 552 can be a thin-wall stainless steel material with a diameter ranging from about 5 mm to 10 mm.

Figure 4B:
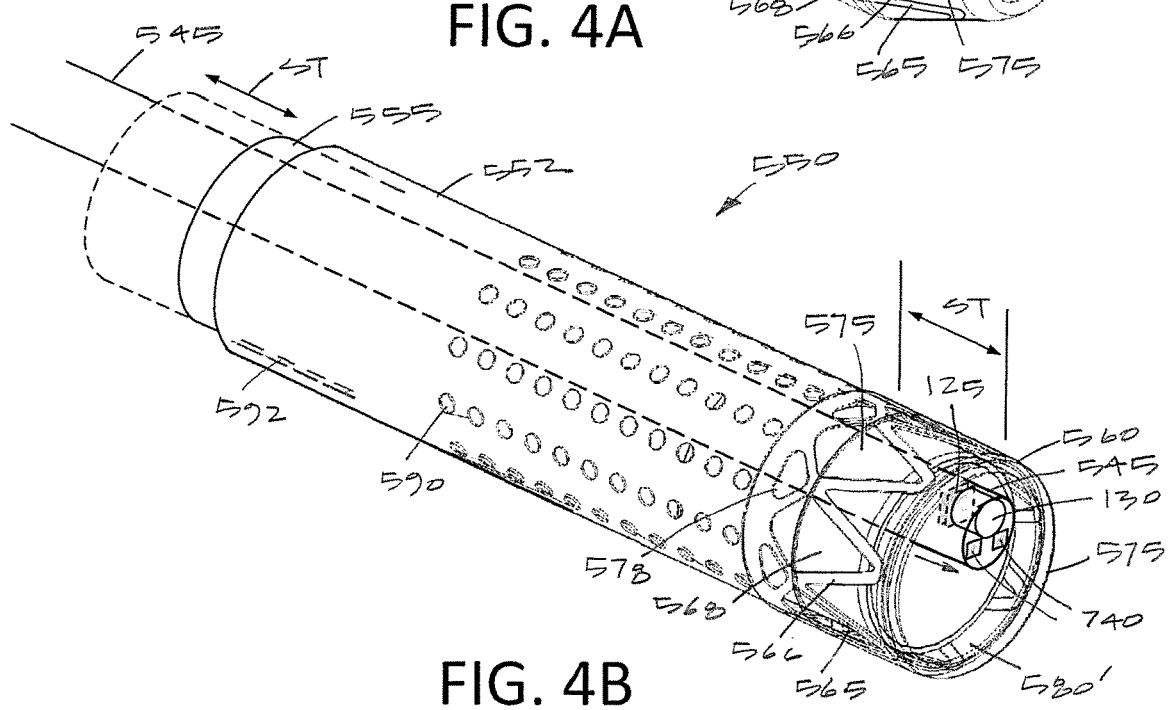
FIG. 4B is another view of the distal end portion of the resecting device of FIG. 4A showing the resilient structure in a second, expanded cylindrical shape for introduction of a resecting component therethrough.

In FIG. 4A, which is an enlarged view of the resilient structure 560 of FIGS. 1 and 2 in its tapered position, it can be seen that the structure 560 is in a repose, or non-tensioned and contracted configuration. FIG. 4B show the distal end 558 of the sleeve assembly and resilient structure 560 in a tensioned and expanded configuration.

In FIG. 4A, it can be seen that one variation of outer introducer sleeve 552 comprises a thin-wall metal tubing with a distal portion 565 that comprises a spring material that defines a plurality of spring struts 566 and openings 568 to allow movement of the structure 560 from the repose position of FIG. 4A to the tensioned position of FIG. 14B. In one variation, the struts 566 define triangular shapes around openings 568 and the struts can range in number from about 4 to 20 or more. In a typical embodiment, the struts 566 are fabricated by cutting the thin-wall tubing of a spring material and then forming the struts 566 into the repose shape as shown in FIG. 4A. In another variation, the struts can be formed from a round, flat or oval spring-type wire elements. The spring elements then can be welded or otherwise bonded to the distal end 570 of the rigid sleeve portion indicated at 572.

As can be further seen in FIGS. 4A and 4B, the resilient structure further comprises an elastomeric material 575, such as silicone, molded over the struts 566. The distal end 572 of the rigid sleeve portion is provided with apertures 578 therein for engaging the over-molded elastomer. In one variation, the elastomer 575 is a substantially transparent material to allow viewing therethrough. In other variations, the elastomer or polymer material may be opaque or non-transparent. The tapered shape of the resilient structure 560 in FIG. 4A is configured with a distal opening 580 that has a selected dimension that may range from 10% to 50% of the diameter of the opening 580' of the structure 560 in its expanded shape as shown in FIG. 4B. The dimension of the distal opening 580 in the tapered position of FIG. 4A is selected to allow viewing therethrough with the imaging sensor 125 during insertion of the distal end of the device 100 through a body passageway.

As can be seen in FIGS. 4A and 4B, in one variation the endoscope sleeve 545 can be in a proximal position when the resilient structure 560 is in its contracted, tapered configuration and then the endoscope can be move distally when the resilient structure 560 is in its open, tensioned position as shown in FIG. 4B.

Figure 3:
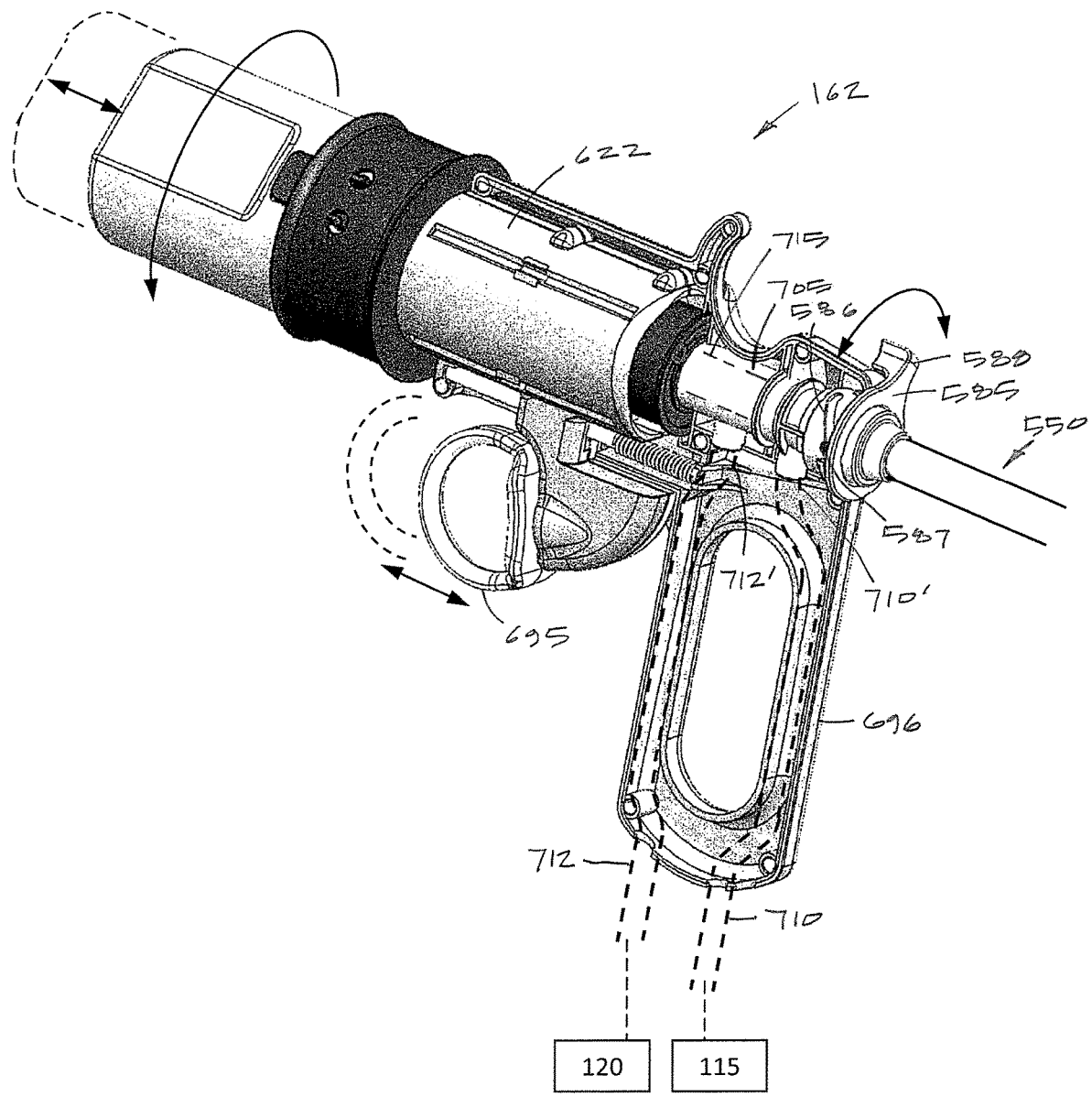
FIG. 3 is a perspective view of a handle of the resecting device of the system of FIGS. 1-2.

FIGS. 1-3 show the mechanism for moving the resilient structure 560 from the tapered, contracted position of FIG.

Figure 5:
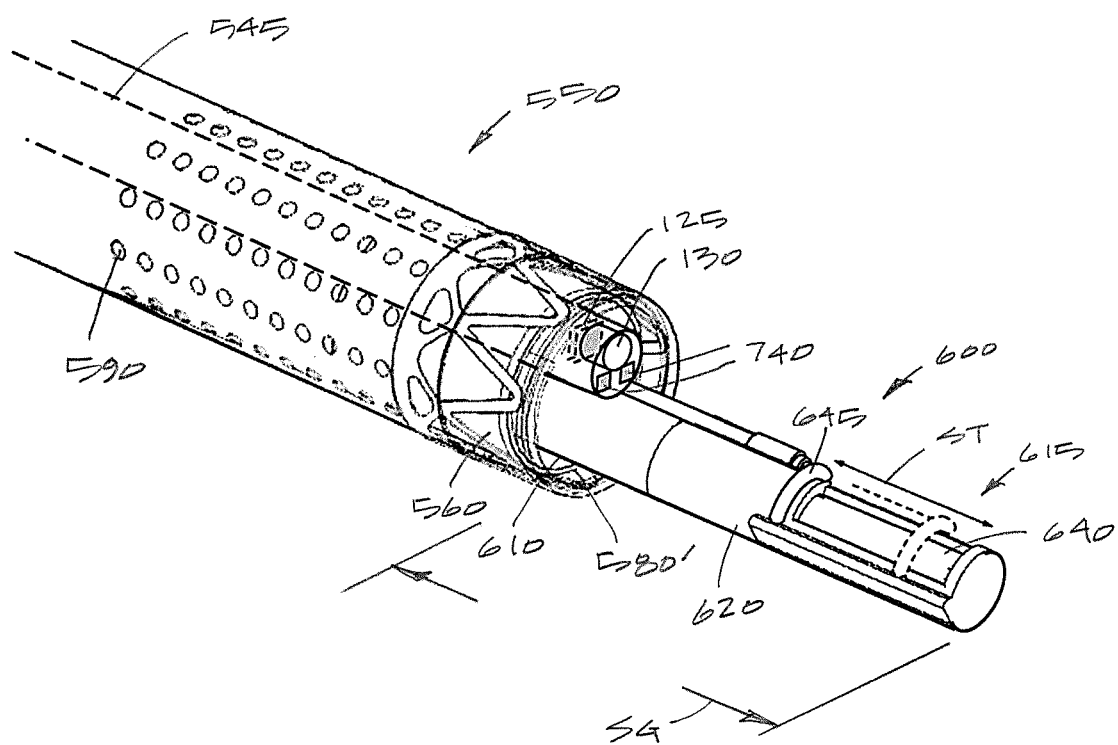
FIG. 5 is a view of the distal end portion of FIG. 4B in its expanded cylindrical shape with a resecting component extending distally beyond the resilient structure.

4A to the cylindrical position of FIG. 4B. In FIG. 3, it can be seen that the introducer sleeve assembly 550 includes the inner sleeve 555 that is adapted to move axially from a retracted position to the extended position as shown in FIGS. 4B and 5. In other words, the distal movement of the inner sleeve 555 will contact the inner surfaces 582 of the struts 566 and elastomeric material 575 in the tapered position of FIG. 4A and then push the struts 566 outwardly and stretch the elastomeric material 575 to provide the cylindrical shape of FIGS. 4B and 5 as the inner sleeve 555 is fully extended. FIG. 4B shows that the stroke ST of inner sleeve 555 can range from about 5 mm to 20 mm in a typical embodiment.

Figure 9:
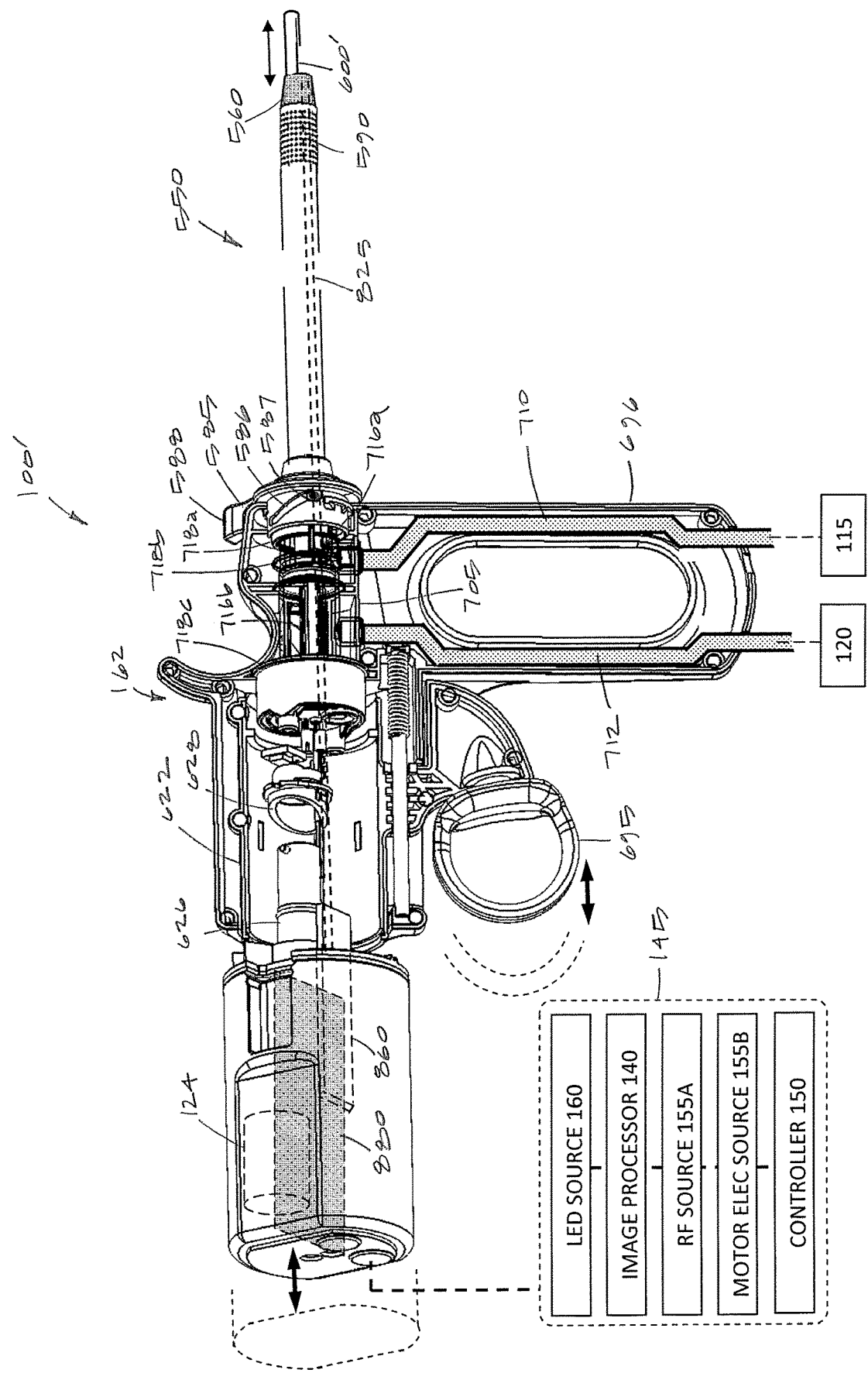
FIG. 9 is a perspective view of a handle of another resecting device that is very similar to that of FIGS. 1-2 except the working end or the tissue-resecting component is different and is shown in FIG. 10.

Referring to FIGS. 1, 3 and 9, the mechanism for moving the inner sleeve 555 from its retracted position to its extended position of FIG. 4B can be understood. In FIGS. 3 and 9, it can be seen that a rotating actuator element 585 is provided which has a cam surface 586 which interfaces with an element 587 of the inner sleeve 555 to move the inner sleeve 555 axially back and forth upon rotation of the finger tab 588 as indicated by arrow AA in FIGS. 1-3. Thus, the finger tab 588 can be designed to move from approximately 45° to 90° to move the inner sleeve 555 in the desired stroke ST as shown in FIG. 4B.

Figure 6:
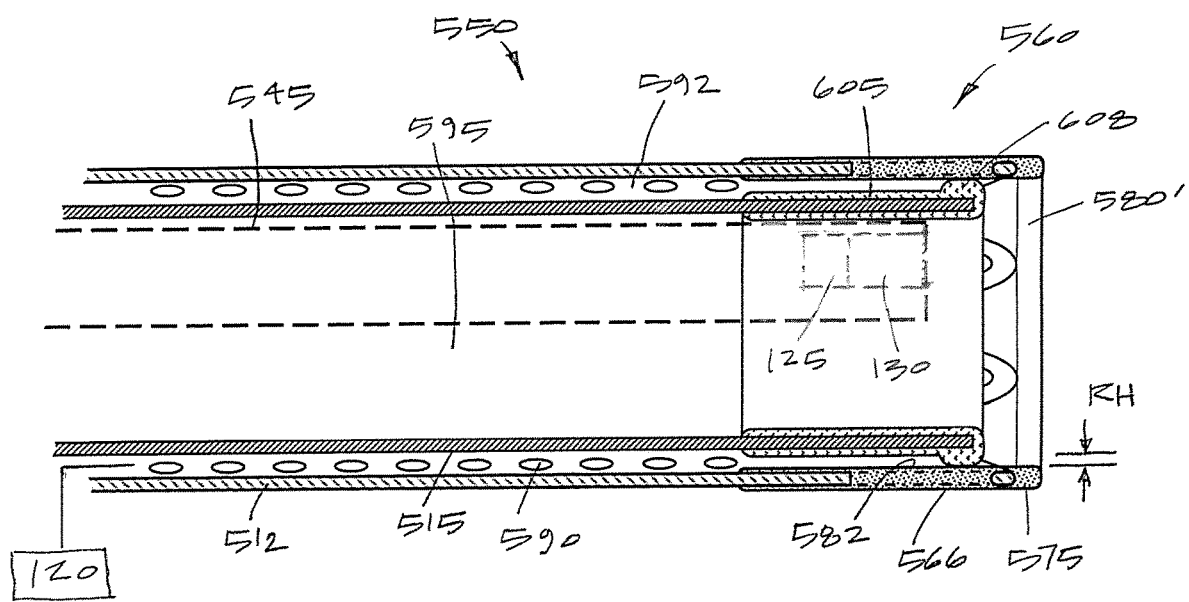
FIG. 6 is a sectional view of the distal end portion of the resecting device and resilient structure of FIG. 4B taken along line 6-6 of FIG. 4B.

Now turning again to FIG. 4A, in another aspect of the invention, the outer introducer sleeve 552 is configured with a plurality of ports 590 which communicate with the annular space 592 between the outer sleeve 552 and the inner sleeve 555 (see FIG. 6). In one variation, the annular space or outflow channel 592 between the inner and outer sleeves 552, 555 communicates with the negative pressure source 120 and thus provides an outflow path for distention fluid which may be independent of the flow channel through the resecting component 600. In the variation shown in FIGS. 4B and 5, the sleeve assembly 550 has a fluid inflow channel 595 that comprises the space outward of the shaft 610 of the resecting component 600 and within the inner sleeve 555.

In FIG. 6, it can be seen that the distal portion of the inner sleeve 555 includes a polymer over-molded portion 605 (e.g., silicone) which serves two purposes. First, the polymer over-molded portion 605 has an annular ridge 608 which interfaces with the inner surfaces 582 of the struts 566 and elastomeric material 575. The radial height RH of the annular ridge 608 thus provides the annular space 592 between the outer surface of the inner sleeve 555 and the inner surface of the outer sleeve 552 through which distention fluid may be aspirated after flowing through the multiple ports 590 in the outer sleeve 552. Secondly, the annular ridge 608 of the over-molded polymer portion 605 can be adapted to seal the interface between the inner sleeve 555 and the resilient structure 560 so that distention fluid is not aspirated through the distal opening 580' of the resilient structure 560 in its cylindrical shape as shown in FIG. 6. This aspect of the invention may be useful to prevent any interference with inflows of distention fluid through inflow channel 595. Rather, the variation shown in FIGS. 5 and 6 allows for fluid inflows to exit the resilient structure 560 and opening 580' around the distal end of the endoscope sleeve 545 which provides the advantage of clearing the visual field distal to the endoscope sleeve 545 to thereby maintain clear viewing. If both inflows and outflows were adjacent to one another in the interior of the resilient structure 560, the clearing of the visual field with fluid inflows could be impaired. In another variation (not shown), the annular ridge 508 could be provided with notches to allow a portion of the fluid outflows into annular space 592 to flow through the distal opening 580'. In a typical embodiment, the negative pressure source 120 would communicate with both the annular space 592 and the aspiration channel 525 in the resecting component 600.

Figure 7:
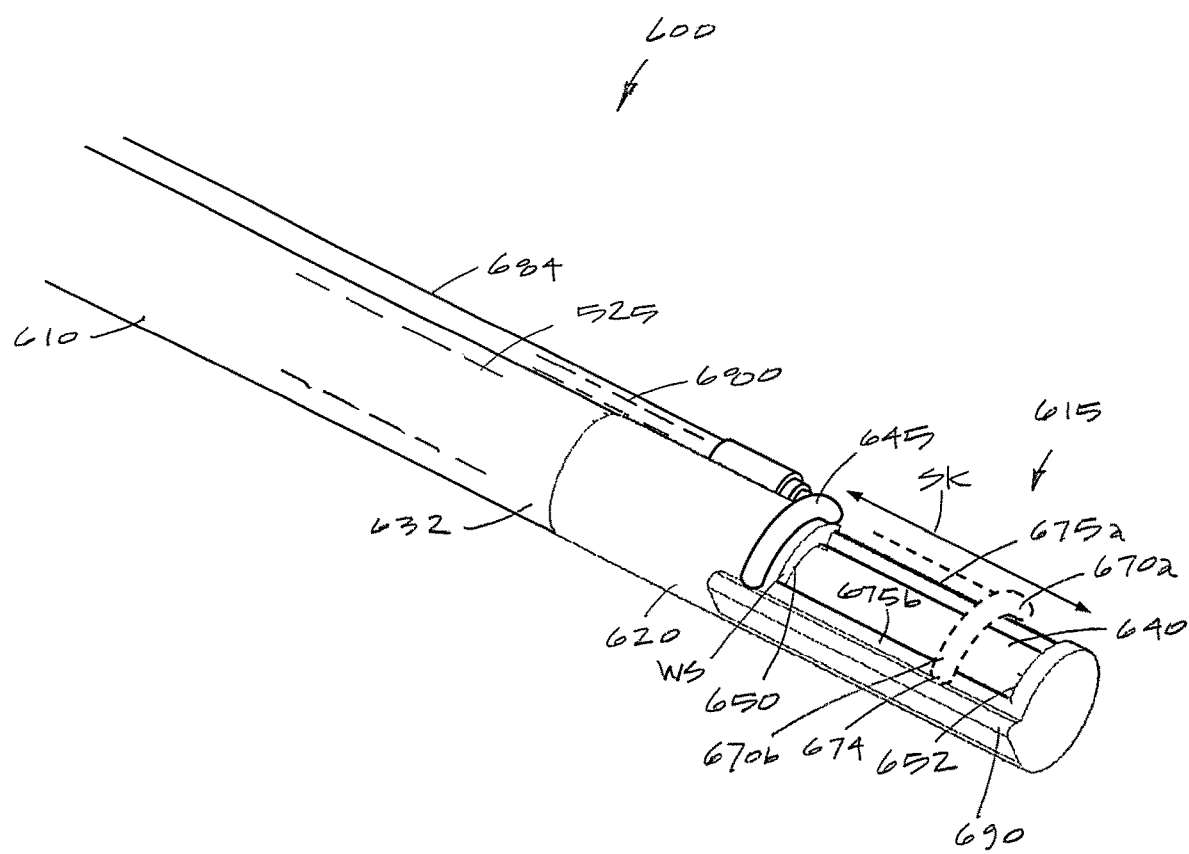
FIG. 7 is a perspective view of the working end of a shaft of the tissue-resecting component also shown in FIG. 2, the component having a distal dielectric housing and a reciprocating electrode that is adapted to move axially across the outer surface of a tissue-receiving window.
Figure 8:
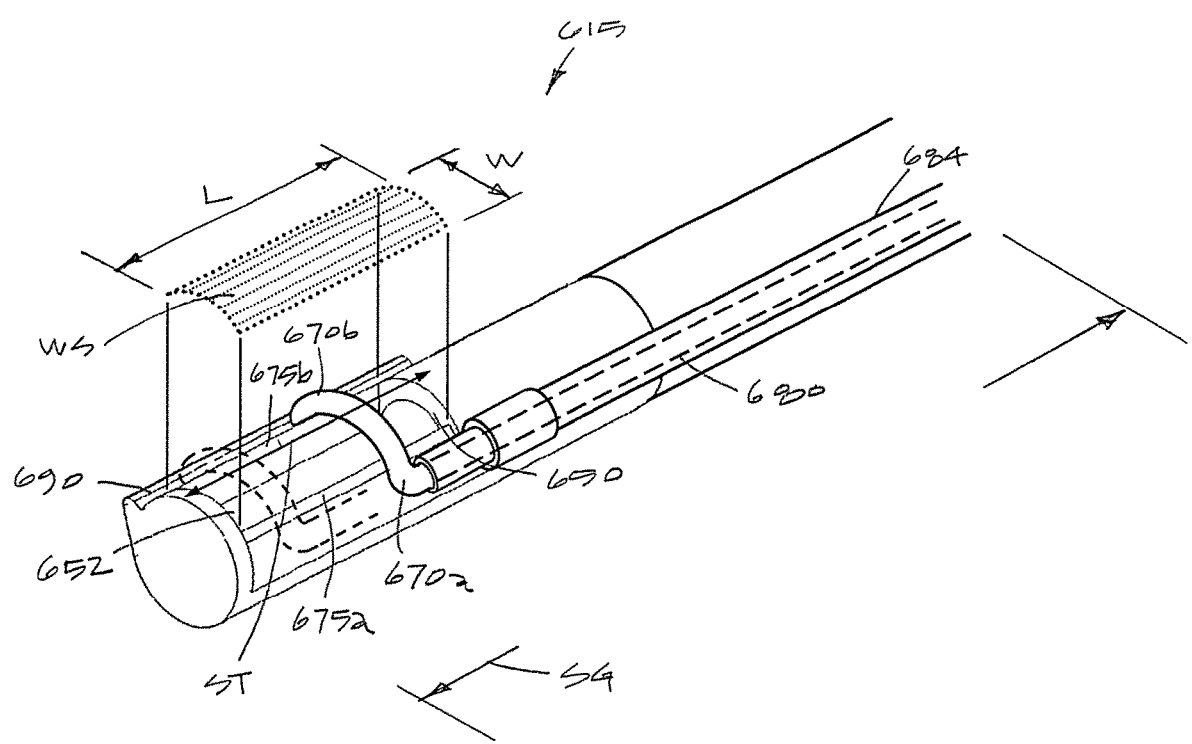
FIG. 8 is another perspective view of the working end of FIG. 7 from a different angle.

FIGS. 5, 7 and 8 illustrate an electrosurgical tissue-resecting component 600 that is carried in the introducer sleeve assembly 550. The elongated shaft or extension portion 610 has an outer diameter ranging from about 2 mm to 6 mm, and in one variation is about 4 mm to 5 mm in diameter. The shaft 610 extends about its central longitudinal axis 612 to its working end 615 that typically comprises a dielectric housing 620 as can be seen in FIGS. 7 and 8.

The proximal end 621 of the shaft 610 is coupled to the rotatable core 622 shown in FIGS. 1 and 2. A motor drive unit 624 shown in FIGS. 1 and 2 is adapted to reciprocate the electrode 645 as will be described further below. The reciprocation mechanism can be of any type known in the art and FIG. 9 shows a rotating drive sleeve 626 coupled to the motor drive 124 that has a surface (not shown) that rotates against a cam surface 628 coupled to a elongate shaft element connected to the electrode 645. It should be appreciated that the core 622 can be rotated 360° within the handle 162 which will not only rotate the resecting component but also rotate the image sensor 125 positioned at the distal end of the introducer sleeve assembly 550.

Referring to FIG. 7, in general, it can be seen the working end 615 includes the distal end portion 632 of shaft 610 that is coupled to the dielectric housing 620 which has a curved or part-cylindrical surface that has a tissue-receiving window 640 therein. A moveable electrode 645 is adapted to be driven by a motor drive unit 624 in the handle 162 (see FIG. 1) so that the curved electrode 645 can reciprocate across the window 640 from a proximal window end 650 to a distal window end 652 to thereby electrosurgically resect tissue that is captured in the window 640. The targeted tissue can be suctioned into and captured in window 640 by means of a negative pressure source 120 operated by controller 150 that communicates with a tissue extraction channel or aspiration channel 525 extending through the shaft 610 and connects to the window 640.

FIGS. 7 and 8 illustrate the dielectric housing 620 that can comprise a ceramic material such as zirconium oxide, aluminum oxide, silicon nitride or similar materials as are known in the art. Alternatively, the dielectric housing 620 can comprise at least in part a polymer or a glass material. In FIGS. 7-8, it can be seen that window surface has a curvature from side to side that can generally can match the diameter of shaft 610. Correspondingly, the electrode 645 is curved to cooperate with the window surface wherein an inner electrode surface has a radius ranging from 1 mm to 3 mm.

As can be further be seen in FIGS. 7-8, the width W of the window 640 can range from about 2 mm to 6 mm and the window length L can range from about 4 mm to 10 mm. Referring to FIGS. 7-8, one variation of tissue-resecting component 605 has an electrode 645 that can be tungsten or stainless steel wire that with curved electrode adapted to reciprocate across the window 640 at any suitable rate and in an embodiment can range from 10 to 20 Hz or more.

Referring to FIG. 8, in one variation of dielectric housing 620, it can be seen that the electrode 645 has a first lateral side 670a and a second lateral side 670b that extends to electrode tip 674. Thus, when moving axially, the lateral sides 670a and 670b of electrode 145 extend across the lateral sides or edges 675a and 675b of the window 640 to ensure that any tissue captured in the window is resected as the electrode 645 passes the window edges to function like a shear to resect tissue in a scissor-like manner. Further, the stroke SK is adapted cause the electrode 645 to reciprocate across the proximal window end 650 and the distal window end 652 as described above to electrosurgically shear tissue captured in window 640.

Referring to FIG. 7, the electrode 645 is coupled to wire shaft member 680 that extends through sleeve 682 that comprises a portion of the outer surface of shaft 610. The wire shaft member 680 is covered with an insulator sleeve 684 to thus provide an active electrode 645 with limited surface area which lower RF power requirements. The device can include a footswitch or finger switch (not shown) for activating the device wherein such activation would energize the electrode 645 from RF source 160 and also activate the motor drive 624.

Referring again to FIG. 3, the housing 620 is configured with a ledge 690 adjacent the lateral edge 675b of the window to receive and abut the distal tip 674 of electrode 645 as it reciprocates. The ledge 690 is adapted to prevent the electrode tip 674 from being snagged or caught in tissue.

FIG. 5 shows the introducer sleeve assembly 550 and the resilient structure 560 in its expanded position with the working end 615 of the resecting component 600 advanced through the distal the opening 580' in the resilient structure 560. As can be understood from FIGS. 2 and 5, the working end of the resecting component 600 is axially movable over stroke SG by means of actuating the thumb grip 695 axially relative to the fixed pistol grip portion 696 of the handle 162 (FIG. 2). At the same time, electrode 645 can be reciprocated to resect tissue as a physician axially and/or rotationally moves the working end 615 of the resecting component 600.

FIG. 8 shows working end 615 of the resecting component 600 from a different angle. In this variation, it can be seen that the window 640 of the working end defines the window surface WS or curved plane across which the electrode 645 reciprocates and cuts tissue. In this variation, the window 640 has a substantially large surface area WS for interfacing with targeted tissue, and the reciprocating electrode 645 in a typical procedure can provide a tissue removal rate that is greater than 5 grams per minute.

As can be understood from FIGS. 1 and 2, the fluid management component 110 includes a fluid source 115 and the negative pressure source 120. Typically, the fluid source comprises a saline bag and a peristaltic pump (not shown) controlled by the controller 150 for providing pressurized inflows into a working space. The negative pressure source 120 is provided typically by a second peristaltic pump controlled by the controller 150 to aspirate fluid and tissue chips through the device into a collection reservoir. Such systems are known in the art and need not be described further herein.

FIGS. 1, 3 and 9 illustrate the inflow and outflow pathways in the interior of the resecting device 100 or 100' which are coupled to the inflow and outflow pumps of the fluid management component 110 (FIG. 1). As can be seen in FIGS. 3 and 9, a flow channel housing 705 is provided in the handle 162 which includes means for allowing rotation of the rotating core 622 while maintaining the inflow and outflow channels in the sleeve assembly 550 in communication with inflow tubing 710 and outflow tubing 712. It can be seen in FIGS. 3 and 9 that the rotating shaft portion 715 within the flow channel housing 705 includes annular channels 716a and 716b with seals 718a, 718b and 718c therebetween, wherein annular channel 716a communicates with the inflow tubing 710 connected to housing 705 and further communicates with the inflow channel 595 in the sleeve assembly 550 (FIG. 6). Annular channel 716b communicates with the outflow tubing 712 connected to housing 705 and further communicates with the outflow channel 592 in sleeve assembly 550 (FIG. 6). Thus, it can be understood that the rotating shaft portion 715 within the flow channel housing 705 allows for fluid inflows and outflows as the core 622 core is rotated.

Now turning to FIGS. 4A and 5, the endoscopic viewing component comprises the distal imaging sensor 125 and lens 130 carried at the end of the endoscope sleeve 545. The endoscope sleeve 545 typically may be axially translatable within the shaft as shown in FIGS. 4A-4B. The mechanism for advancing the endoscope sleeve 545 can be thumb grip 695 which advances the endoscope sleeve 545 a predetermined distance and then stops its advancement. Further advancement and retraction of the thumb grip 695 then is adapted to translate the working end 615 of the resecting component 600 back and forth. In one variation, the endoscope sleeve 545 comprises a thin-wall tubular member of a (e.g., a metal or polymer) with the image sensor 125 and lens 130 positioned in a distal end thereof. A plurality of electrical conductors 722 are carried in passageway 724 of the sleeve 545 that are coupled to the image sensor 125. The conductors 722 can be in a flex circuit or can be in any suitable cable. Such conductors 722 carry signals from the image sensor to the image processor 140 which is in the base unit 145 but optionally can be carried in the handle 162. The entire sleeve 545 and lens 130 is encased in an insulator coating or shielding 725 that has sufficient insulative strength to shield the image sensor 125 and signals carried. by conductors 722 from any potential electrical interference from RF current carried to the working end of the resection device or from current carried to the motor 124. The insulator coating 725 is a type that is transparent for covering the lands 130 to allow viewing therethrough. In one variation, the insulator coating 725 extends over the entire length of the sleeve 525 as well as over any length of the conductors 722 that extend through the handle 162. The image sensor 125 may be any electronic imaging chip known in the art with a suitable lens 130 which are available, for example, from OmniVision, 4275 Burton Drive, Santa Clara, CA 95054 such as a High Definition Sensor used in cell phones and laptops.

In one variation, still referring to FIGS. 4B and 5, the endoscopic sleeve 545 further includes at least one LED 740 or other light source carried at the distal end of the sleeve. Of particular interest, the rotating core 622 is adapted to carry the image sensor 125 and the LEDs 740 together with the resecting component 600 thus allowing 360° rotation. Electrical leads 742 are also carried in the passageway 724 of the sleeve 545 which extend to LED source 160 (FIG. 1). The shielding 725 described above also protects the LEDs from interference by the RF source or motor source.

Figure 10:
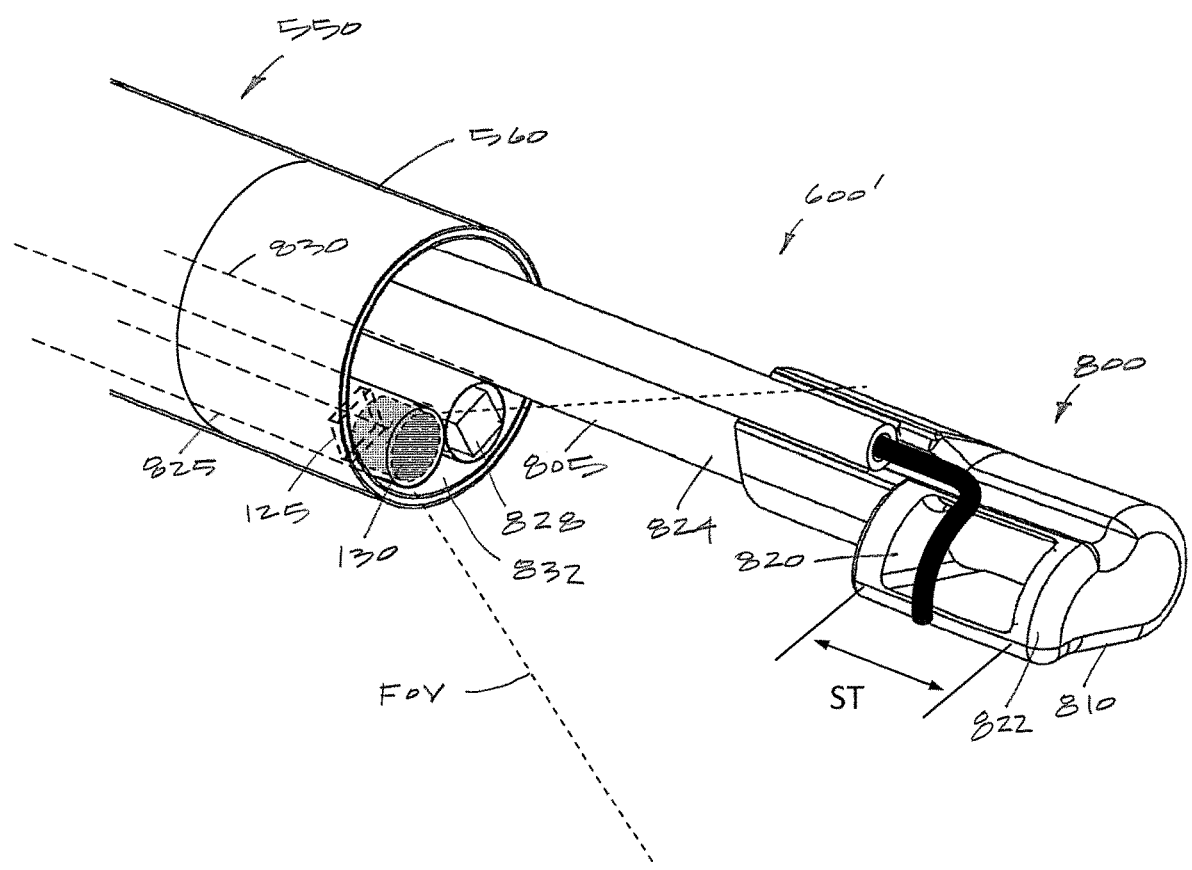
FIG. 10 is a perspective view of the variation of a working end of a tissue-resecting component of FIG. 9 with a reciprocating electrode.
Figure 11:
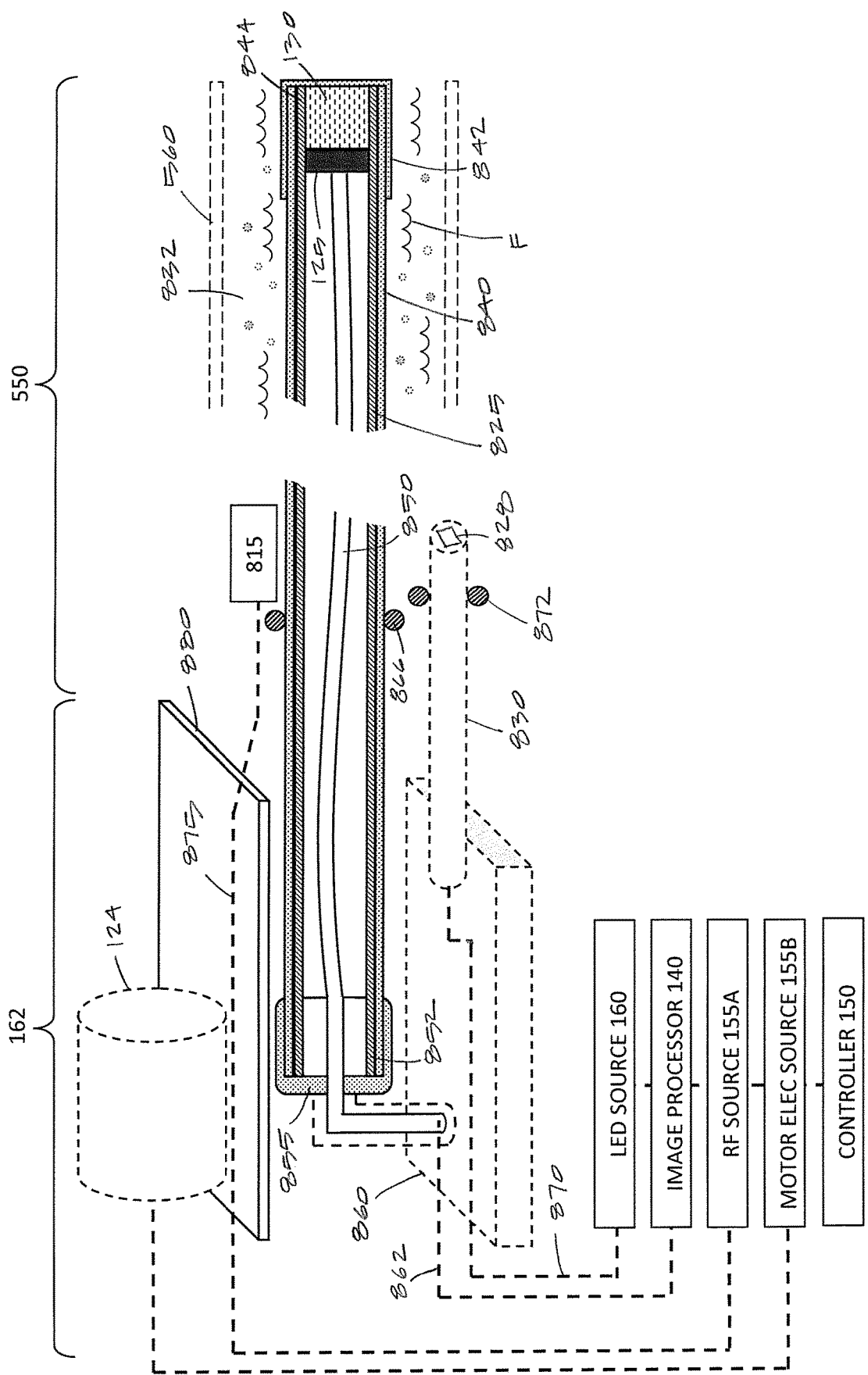
FIG. 11 is a schematic view device of FIGS. 9 and 10 showing the endoscopic viewing component and electromagnetic shielding that encases the viewing component as well as an LED component.

Now turning to FIGS. 9, 10 and 11, another variation of resecting device 100' is shown which is similar to that of FIGS. 1-6 except the resecting component 600' has a different variation of a working end 800. The working end 800 of the RF tissue-resecting component 600' again has an elongated extendable shaft 805 that carries a dielectric housing 810 with a reciprocating electrode 815 (see FIG. 10). In this variation, the dielectric housing 810 which carries the window 820 has an offset portion 822 that is outward from the cylindrical surface 824 of the elongated shaft 805 the resecting component. In this variation, the offset window 820 and electrode 815 allows for improved endoscopic viewing of the electrode 815 when being reciprocated. The stroke of the electrode 815 is indicated at ST which is then easily observed within the field of view FOV (see FIG. 10).

FIGS. 10 and 11 show that the image sensor 125 and lens 130 are carried in a first independent tubular sleeve 825 in this variation. Similarly, the single LED 828 is carried in a second independent tubular sleeve 830 in the introducer sleeve assembly 550. The use of independent sleeves 825 and 830 allow for compact design while still allowing for fluid outflow channel 832 around the sleeves 825, 830.

FIG. 11 is a schematic view of device handle 162, sleeve assembly 550 and the first tubular sleeve 825 that carries the image sensor 125 and lands 130. The schematic view of FIG. 11 illustrates more details of the electromagnetic shielding around the sleeve 825. It can be seen that a dielectric layer 840, such as a heat shrink tubing, is provided around the entire length of the metal or other electrically conductive sleeve 825 which extends into the handle as can be seen in FIG. 9. In one variation, the dielectric layer 840 is PET having a thickness of at least 0.001" or at least 0.002". The electrically conductive sleeve 825 provides the desired electrical shielding while the dielectric layer electrically isolates the sleeve. Further, another cap layer 842 of a transparent dielectric shielding material can extend around the lens 130 at the distal end 844 of the sleeve 825. Such a cap layer 842 can be bonded with adhesives or other sealing means to the tubular dielectric layer 840. Alternatively, the lens can be configured with a dielectric surface (e.g., glass or polymer) to provide an adequate dielectric layer. FIG. 11 further shows electrical conductors 850 extending from the image sensor 125 through the elongated sleeve 825 to the proximal end 852 thereof which is also encased in a cap layer 855 the dielectric material. The electrical conductors can be in a co-axial cable with dielectric layers around each conductor or it can be a flex circuit. Electrical conductors 850 are then connected to a circuit board 860 carried in the handle 162 of the device as can be seen in FIG. 9. An insulated electrical cable 862 carries image signals from the circuit board 860 to the image processor 140. By this means, can be seen that the signal carrying electrical conductors 850 are encased in electromagnetic shielding the entire distance from the distal image sensor 125 to the circuit board 860 and thereafter to the remote image processor 140. As shown schematically in FIG. 11, elongated sleeve 825 may be surrounded by fluid outflows F in outflow channel 832 which can aggravate electromagnetic interference, and the dielectric layers 840, 842 and 855 can shield the image sensor 125 and conductors 850 from potential interference since the dielectric material covers all surfaces of the sleeve 825 carrying the image sensor and conductors 850. FIG. 11 further shows a seal 866 around the sleeve 825 that prevents fluid flows into the handle 162.

FIG. 11 also shows the second independent sleeve 830 that carries the LED 828 in a schematic view. It should be appreciated that the second sleeve 830 and LED 828 are encased in shielding of the same type as shown in more detail in FIG. 11 relating to the first independent sleeve 825 that carries the image sensor 125. FIG. 11 shows that electrical conductors 870 extend from the LED source 160 to the circuit board 860 and thereafter to the second independent sleeve 830 to power the LED 828. A fluid seal 872 is also shown schematically around independent sleeve 830 to prevent fluid flows from extending into the handle 162.

Now referring to FIGS. 9 and 11, an additional electrically conductive shielding member 880 is provided in the handle 162 to shield the circuit board 860 from the motor 124 and the electrical cable 875 (FIG. 11) that extends from the RF source 155A to the electrode 815 at the working end 800 of the resecting device 100' (see FIG. 10). Thus, the additional RF shielding member 880 can ensure that the electrical current driving the motor 124 and the resecting device cannot interfere with signals from the image sensor 125.

Figure 12:
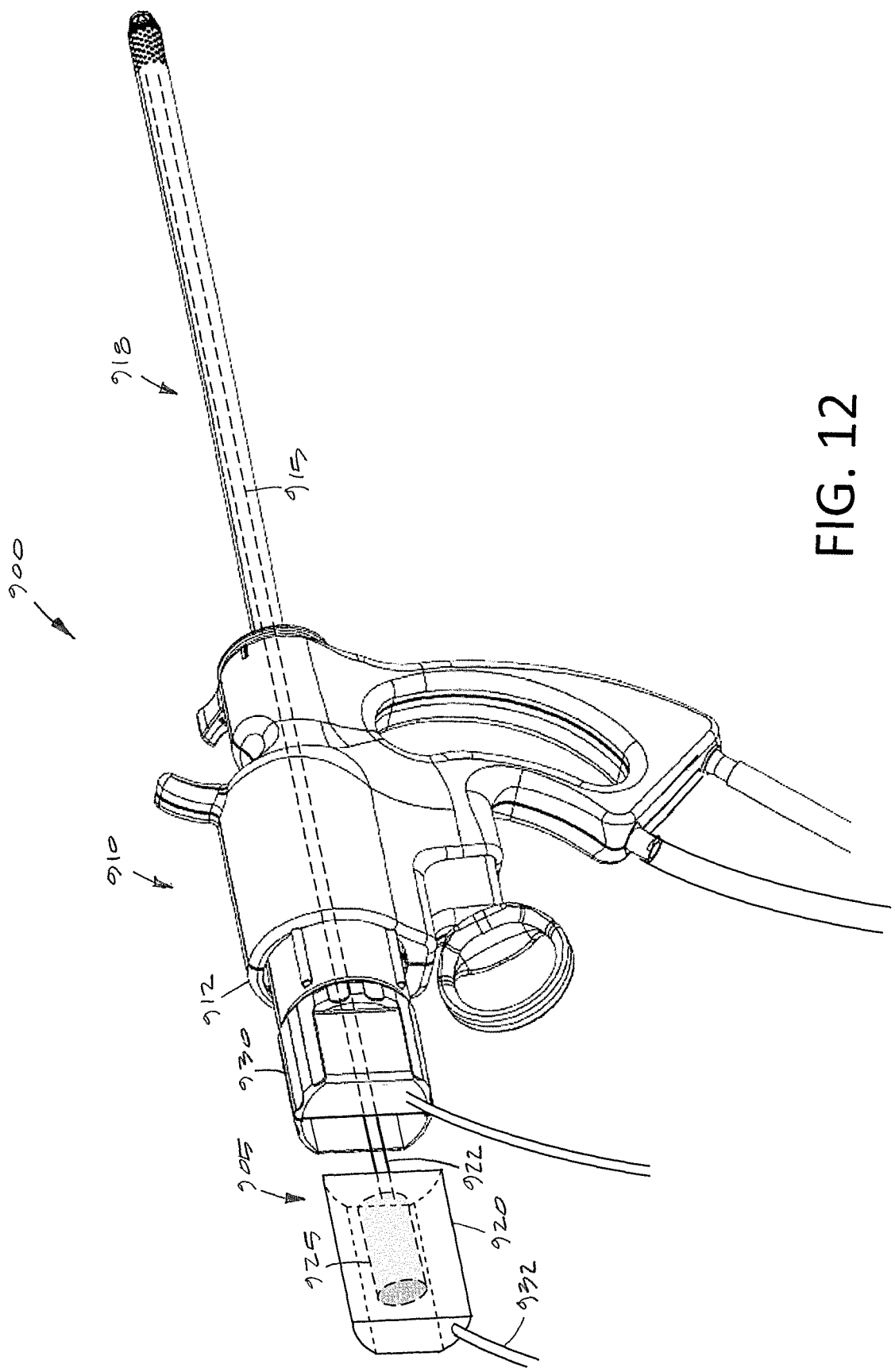
FIG. 12 is another variation of a hand-held system similar to that of FIG. 1 wherein the RF resecting component is removable to allow the endoscope portion to be used in the diagnostic tool or to accommodate a different tool in the open working channel.
Figure 13:
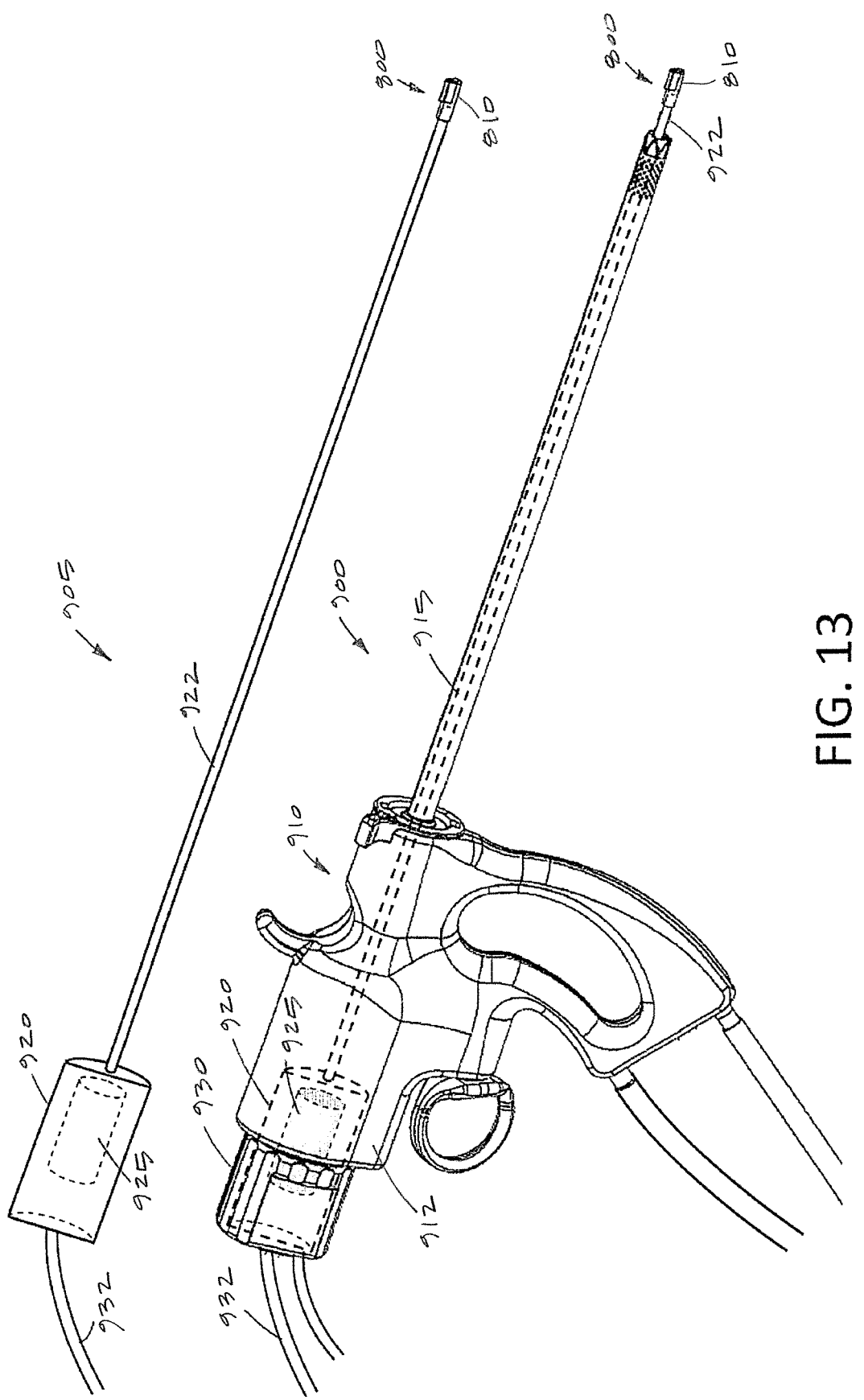
FIG. 13 is another view of the hand-held system of FIG. 12 showing the RF resecting component removed from the handle assembly.

FIGS. 12-13 illustrate another variation of a hand-held tissue resecting system 900 that is similar to that of FIG. 1 except in this embodiment, the RF resecting component 905 is separate and removable from the endoscope portion 910 and handle 912. In this variation, the endoscope portion 910 can be used as a diagnostic tool by the physician before electing to insert the resecting component 905 into the assembly. Thus, the system may be used as a diagnostic tool before determining whether the RF resecting component 905 is needed which can make use of the system more economical. Further, the open working channel 915 extending through the shaft assembly 918 can be used to introduce different tools in the event a grasper or a biopsy punch may be needed instead of, or in addition, to the RF resecting component 905.

In FIGS. 12-13, it can be seen that the resecting component thus comprises a proximal housing 920 that carries an electric motor 925 and reciprocation mechanism for reciprocating an electrode as shown in FIG. 10, wherein the proximal housing 920 is coupled to elongated shaft 922 that carries working end 800 as shown in FIG. 10 with dielectric housing 810 and electrode 815. FIG. 12 illustrates that housing 920 is configured for insertion into rotating core 930 of the device. The resecting component 905 has his own independent electrical cable 932 for coupling to the controller 150 and RF power source 155A and motor electrical source 155B (see FIG. 1). In this variation, a fluid seal (not shown) may be needed to prevent fluid flows around the shaft 922 in the proximal direction in the handle 912. The fluid seal can comprise any suitable form of flap valve, duckbill valve, O-ring or the like disposed in the handle 912 and/or on the resecting component 905.

In some variations, the RF component 905 may have aspiration tubing connected to the proximal housing 920 and in other variations, the tissue extraction lumen in the elongated shaft 922 may couple to an aspiration port in the interior of handle 912.

In general, a medical device corresponding to the invention comprises a handle coupled to an elongated sleeve assembly or shaft, an electronic image sensor and at least one LED carried at a distal end of the shaft with electrical conductors extending through the shaft to the image sensor and LED, respectively. The device further has a working channel adapted to receive a removable RF component with motor-driven distal RF electrode for applying energy to tissue. The device further has electromagnetic shielding disposed around the image sensor, LEDs and electrical conductors extending to the image sensor and LEDs were in the shielding is configured to prevent interference from the energized RF component in motor on the function of the image sensor and LEDs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A tissue resecting device comprising:
a handle coupled to an introducer sleeve;
a resecting component with an elongate shaft that is extendable and retractable within a central passage of the introducer sleeve, wherein a working end of the shaft has a tissue-receiving window that opens to a tissue aspiration lumen therein, and a moveable RF electrode positioned over an exterior of the tissue-receiving window to resect tissue;
at least one elongate member disposed within the central passage of the introducer sleeve with a distal end thereof carrying an electronic image sensor and an LED;
electrical leads connected to the imaging sensor and LED disposed in an interior of the at least one elongate member; and
electromagnetic shielding disposed over an exterior of the at least one elongate member to protect the electrical leads, electronic image sensor and LED from electrical interference from electrical current to the RF electrode during use; and wherein the distal end of the introducer sleeve has an atraumatic tip with a repose conical shape that is expandable to a cylindrical shape when subjected to an internally applied radially outwardly acting force.

2. The tissue resecting device of claim 1, further comprising an actuator in the handle to cause movement of the atraumatic tip relative to an interior sleeve to apply said radially outwardly acting force.

3. The tissue resecting device of claim 2, wherein the elastomeric material is transparent.

4. The tissue resecting device of claim 1, wherein the atraumatic tip comprises at least in part an elastomeric material.

5. The tissue resecting device of claim 1, wherein the resecting component is removable from the handle and introducer sleeve.

6. The tissue resecting device of claim 1, wherein the tissue aspiration lumen is configured to be connected to a negative pressure source for suctioning tissue into the tissue-receiving window.

7. The tissue resecting device of claim 1, wherein the moveable RF electrode is motor driven.

8. The tissue resecting device of claim 7, wherein the motor is configured to reciprocate the moveable RF electrode in a stroke that extends the RF electrode over proximal and distal edges of the tissue-receiving window.

9. The tissue resecting device of claim 1, wherein the moveable RF electrode has first and second lateral portions that extend over first and second lateral edges of the tissue-receiving window.

10. The tissue resecting device of claim 1, wherein the working end of the shaft comprises a dielectric housing and the tissue-receiving window is formed in a surface of the dielectric housing.

11. The tissue resecting device of claim 1, wherein the surface of the dielectric housing is offset outwardly from an outer surface of the shaft.

12. The tissue resecting device of claim 1, wherein the tissue-receiving window has a curved surface and the moveable RF electrode has an arcuate shape that conforms to the curved surface of the tissue-receiving window.

13. The tissue resecting device of claim 1, wherein at least a distal portion of the electromagnetic shielding in the field of view of the image sensor is transparent.

14. The tissue resecting device of claim 1, wherein the image sensor is carried at the distal end of a first elongate member and the LED is carried at the distal end of a second elongate member wherein both the first and second elongate members are disposed within the central passage of the introducer sleeve.

15. A tissue resecting device comprising:
a handle coupled to an introducer sleeve extending about a longitudinal axis;
the distal end of the introducer sleeve comprising an atraumatic tip with a repose conical shape that is expandable to a cylindrical shape when subjected to an internally applied radially outwardly acting force;
an actuator in the handle to provide movement of the atraumatic tip relative to an interior sleeve to apply said radially outwardly acting force;
a resecting component with an elongate shaft that is extendable and retractable from the distal end of the introducer sleeve through the atraumatic tip, wherein a working end of the shaft comprises a dielectric housing with a tissue-receiving window opening to a tissue aspiration lumen therein; and
a moveable RF electrode positioned over an exterior of the tissue-receiving window to resect tissue.

16. The tissue resecting device of claim 15, wherein the tissue-receiving window is formed in a surface of the dielectric housing offset outwardly from an outer surface of the shaft.

17. The tissue resecting device of claim 16, wherein the tissue-receiving window has a curved surface and the moveable RF electrode has an arcuate shape that conforms to the curved surface of the tissue-receiving window.

18. The tissue resecting device of claim 15, further comprising an imaging component in the introducer sleeve with a distal image sensor and LED.

19. The tissue resecting device of claim 18, wherein the resecting component and imaging component are rotatable within the introducer sleeve.

* * * * *